United States Patent
Disch et al.

(10) Patent No.: US 9,128,037 B2
(45) Date of Patent: Sep. 8, 2015

(54) TWO-CHANNELED MEASUREMENT APPARATUS

(71) Applicant: SICK AG, Waldkirch (DE)

(72) Inventors: Rolf Disch, Waldkirch (DE); Florian Bruchig, Waldkirch (DE); Pascal Ortwein, Waldkirch (DE)

(73) Assignee: Sick AG, Waldkirch (DE)

( * ) Notice: Subject to any disclaimer, the term of this patent is extended or adjusted under 35 U.S.C. 154(b) by 0 days.

(21) Appl. No.: 14/293,473

(22) Filed: Jun. 2, 2014

(65) Prior Publication Data

US 2014/0361171 A1  Dec. 11, 2014

(30) Foreign Application Priority Data

Jun. 7, 2013 (EP) .................. 13171075
May 21, 2014 (DE) .......... 20 2014 102 369 U

(51) Int. Cl.
| | |
|---|---|
| *G01N 21/01* | (2006.01) |
| *G01N 21/33* | (2006.01) |
| *G01N 21/35* | (2014.01) |
| *G01J 3/427* | (2006.01) |
| *G01N 21/31* | (2006.01) |
| *G01N 21/3504* | (2014.01) |
| *G01J 3/08* | (2006.01) |
| *G01J 3/10* | (2006.01) |
| *G01J 3/42* | (2006.01) |

(52) U.S. Cl.
CPC ............ *G01N 21/3151* (2013.01); *G01J 3/08* (2013.01); *G01J 3/10* (2013.01); *G01J 3/42* (2013.01); *G01J 3/427* (2013.01); *G01N 21/33* (2013.01); *G01N 21/3504* (2013.01); *G01N 2021/317* (2013.01); *G01N 2021/3155* (2013.01); *G01N 2021/3513* (2013.01)

(58) Field of Classification Search
CPC ............... G01J 3/427; G01J 3/08; G01J 3/10; G01J 3/42; G01N 2021/3155; G01N 2021/317; G01N 2021/3513; G01N 21/3151; G01N 21/33; G01N 21/3504
See application file for complete search history.

(56) References Cited

U.S. PATENT DOCUMENTS 3,413,482 A   11/1968   Ling
3,819,277 A    6/1974   Berthelot et al.

FOREIGN PATENT DOCUMENTS

| DE | 1291533 B    | 3/1969 |
| DE |  148385 A1   | 5/1981 |
| DE | 3926090 A    | 7/1991 |
| EP | 0238871 A2   | 9/1987 |
| JP | 07-012726    | 1/1995 |
| JP | 08-247938    | 9/1996 |

*Primary Examiner* — Mark R Gaworecki
(74) *Attorney, Agent, or Firm* — Nath, Goldberg & Meyer; Jerald L. Meyer; Rury L. Grisham

(57) ABSTRACT

The invention relates to a measurement apparatus for the determination of gas concentrations. The apparatus comprises two spectral channels, wherein the channels are separated by a single chopper wheel. The chopper wheel has several functions. On the transmitting side, it brings the light of the two light sources on the same measuring path, on the receiving side it associates the light to the associated receiver; it has its chopper function to use the lock-in technique; and it opens the possibility to implement an easy zero point correction.

9 Claims, 3 Drawing Sheets

Figure 3:
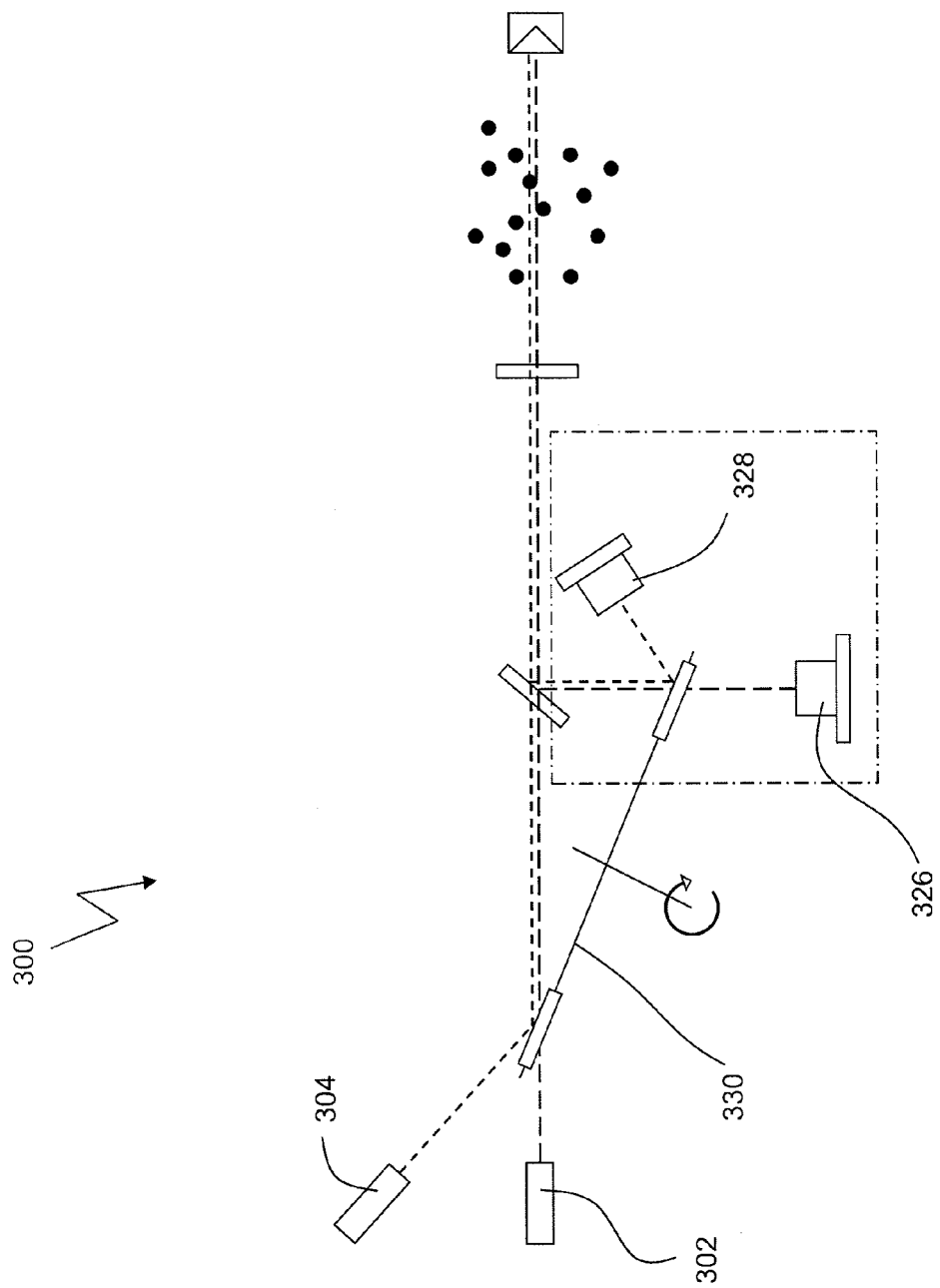

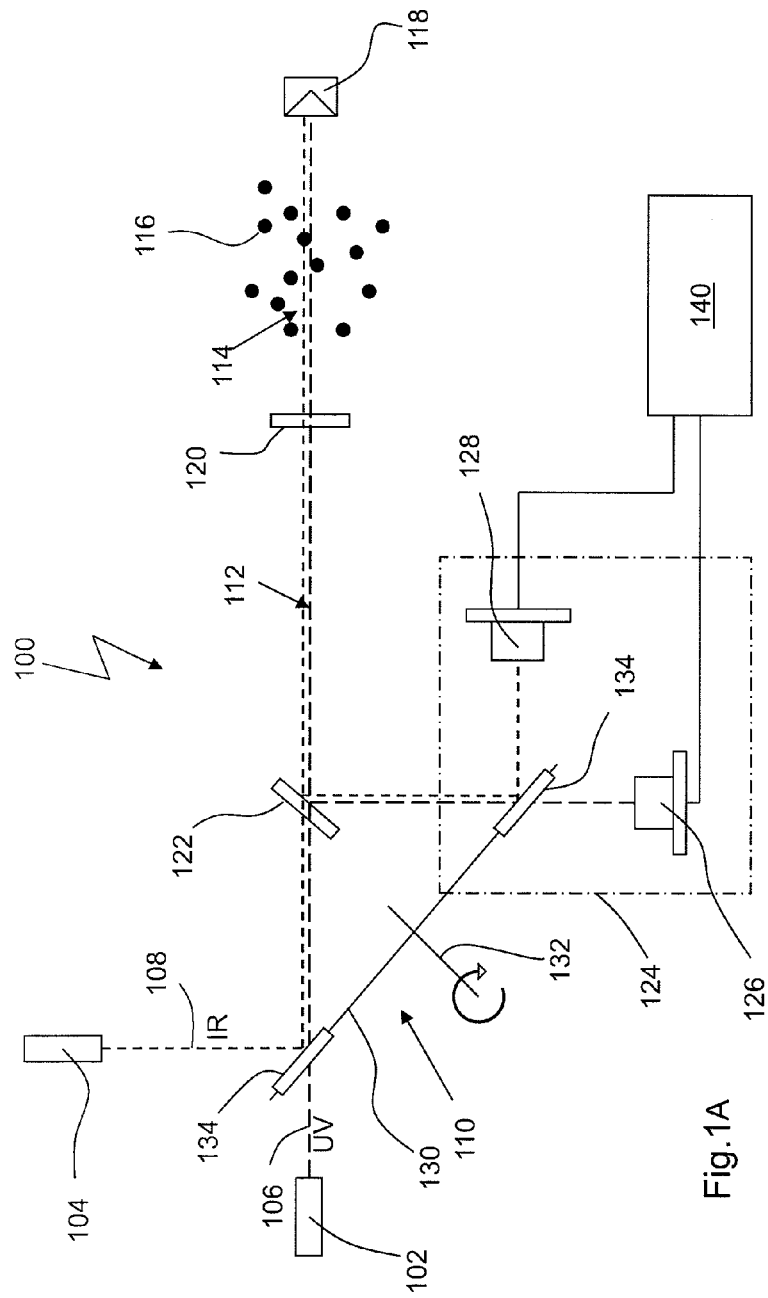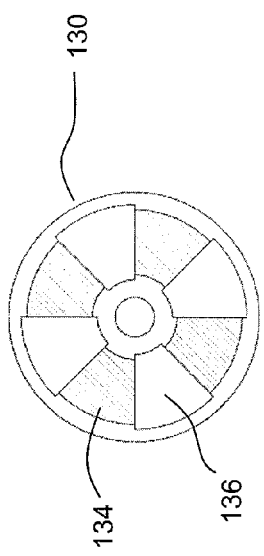
Fig. 1A
Fig. 2A

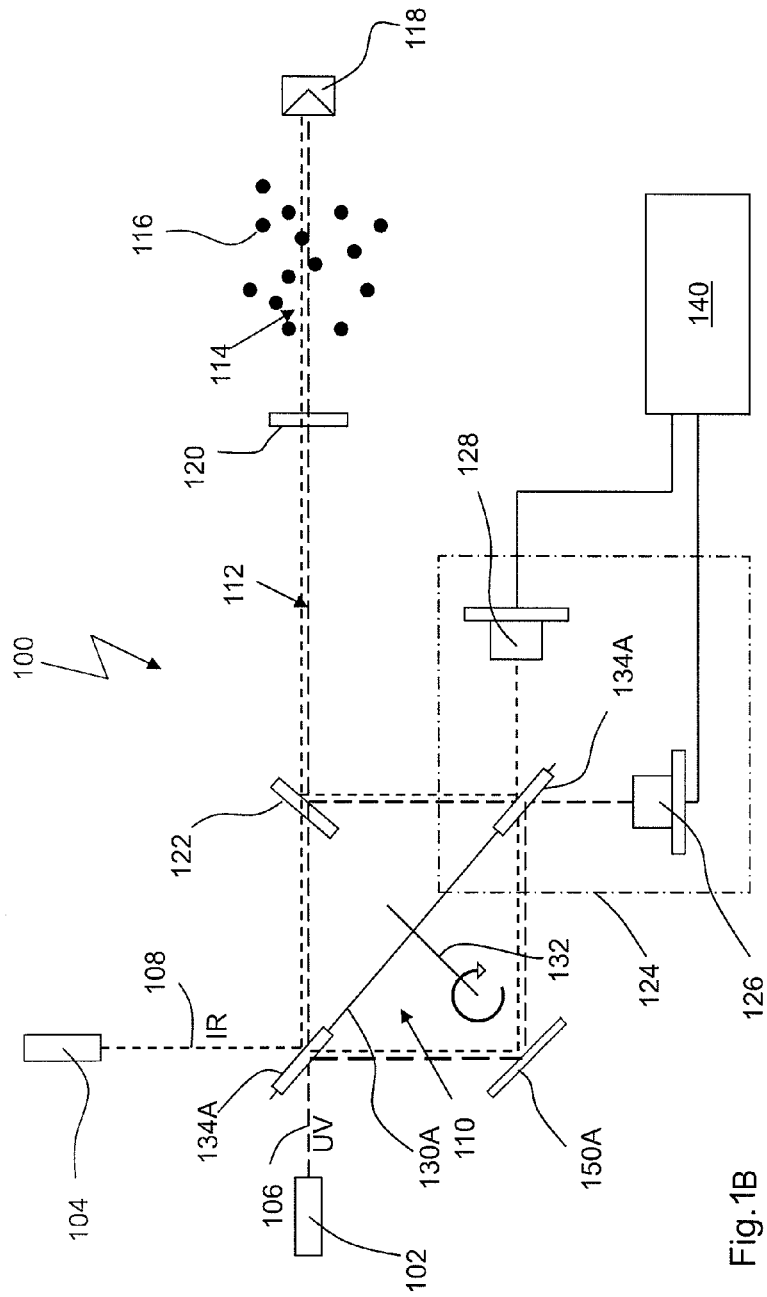
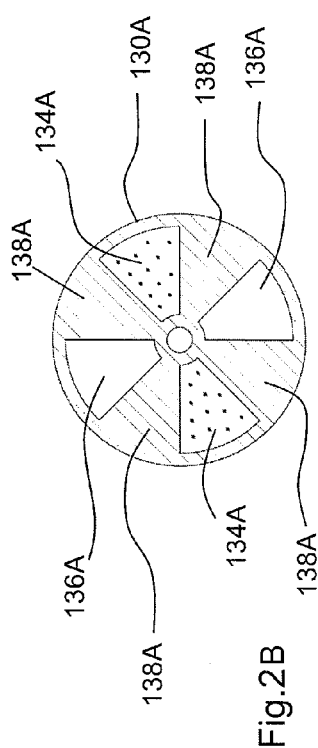
Fig. 1B
Fig. 2B

TWO-CHANNELED MEASUREMENT APPARATUS

The invention relates to a two-channeled measurement apparatus for the determination of gas concentrations comprising a first and a second light source which transmit light of different wavelength ranges into a measurement path; a receiver arrangement which receives the light from the light sources; a chopper apparatus which has two highly reflecting mirrors for one of the wavelength ranges and two cut-outs between the mirrors on the same part circle in the circumferential direction in order to alternately allow the light from the light sources to pass through and/or to deflect the light from the light sources respectively in order to bring the light via the same optical path into the measurement path; and an evaluation unit for the evaluation of the received signals and for the determination of a gas concentration therefrom.

In a measurement apparatus for the determination of gas concentrations in which two spectral channels are combined at an optical path this typically takes place through the use of beam splitters. For this purpose, it is typically required to provide two different light sources at the transmitter side and to combine their light beams coaxially by means of beam splitters and to again divide the spectral components onto (at least) two detectors at the receiver side, this means that one has to align the spectral components back onto different optical paths by means of beam splitters.

The beam splitters are typically configured as geometric or dichroic divider mirrors. The geometric beam splitters can be used over a wide spectral range, however, for each through-passage they bring about an intensity loss of on average 50%. This generally causes very high intensity losses. Having regard to dichroic divider mirrors (or color divider mirrors) the intensity loss is significantly less; however, this solution cannot be realized in dependence on the constellation of the spectral ranges and the through passage ranges permitted.

From the DE 39 26 090 C2, FIG. 4, a measurement apparatus in accordance with the initially named kind is known. In this measurement apparatus the spectral combination takes place by means of a chopper, which has light reflecting sectors and light permeable sectors and an arrangement of hollow mirrors, the arrangement of hollow mirrors being demanding in effort and cost. In this connection "combination" of the beams (spectral channels) in this example only means that the light beams of the light sources are brought onto a common optical path. A separation of the spectral channels does not take place. Rather more a spectral separation takes place in a monochromator to which the light of both light sources is supplied in the same manner and which carries out a spectral division for the separate detection thereof. It is a disadvantage, amongst other things, that the assembly is demanding in effort and cost, firstly due to the large number of hollow mirrors and secondly due to the comprehensive requirements with respect to alignment. Furthermore, the monochromator can generally only record a limited wavelength range and the light yield for the different wavelengths is limited.

DE 1 291 533 A in its FIG. 4 discloses a spectrometer in which the light of one light source is guided once at an optical path by means of a chopper wheel and in dependence on the angular position of the chopper wheel, the optical path leading via a reference cuvette and secondly, at a different time, the light of one light source is guided at an optical path which leads over a measurement cuvette. The same chopper wheel also combines the two beam paths onto a light receiver. Thus, depending on the angular position of the chopper wheel either a reference measurement or a measurement of the measurement gas is recorded.

U.S. Pat. No. 3,413,482 A discloses a spectrometer in which, in the embodiment of the FIG. 2 disclosed there, the light of two light sources is guided onto the same optical path by means of a chopper wheel in such a way that, depending on the angular position of the chopper wheel, on the one hand, the light of the one light source runs through the measurement cell and for a different position the light of the other light source runs through the measurement cell.

EP 0 238 871 A2 discloses a measurement apparatus for exhaust gas analysis in which a plurality of light sources are used for the analysis of different gas components.

DD 148 385 A1 discloses a spectrometer having a chopper wheel which brings about a division of the beam path into a reference beam path and into a measurement beam path.

U.S. Pat. No. 3,819,277 discloses a measurement device comprising a first and a second light source which transmit light of different wavelength ranges into a measurement path; a receiver arrangement which receives the light from the light sources; a chopper apparatus which has two highly reflecting mirrors for one of the wavelength ranges and two cut-outs between the mirrors on the same pitch circle in the circumferential direction in order to alternately allow the light from the light sources to pass through and/or to deflect the light from the light sources respectively in order to bring the light via the same optical path into the measurement path; and an evaluation unit for the evaluation of the received signals and for the determination of a gas concentration therefrom.

Starting from this prior art it is the object of the invention to provide an improved two-channeled measurement apparatus which is of simple design and in which only small light intensity losses arise.

This object is satisfied by a measurement apparatus having the features of the claim 1.

The measurement apparatus in accordance with the invention for the determination of gas concentrations comprises:
  two spectral channels;
  a first and a second light source which transmit light of different wavelength ranges onto a common measurement path;
  a receiver arrangement which receives the light of the light sources;
  a chopper apparatus which has two highly reflecting mirrors for one of the wave-length ranges and two cut-outs between the mirrors on the same pitch circle in the circumferential direction in order to alternately allow the light from the light sources to pass through and/or to deflect the light from the light sources respectively in order to bring the light via the same optical path into the measurement path;
  an evaluation unit for the evaluation of the received signals and for the determination of a gas concentration therefrom;
  wherein the receiver arrangement has a first and a second receiver, wherein the first receiver is associated with the first light source and the second receiver is associated with the second light source for the reception of the light of the corresponding wavelength; and
  wherein the chopper apparatus is designed as a single chopper wheel and the mirrors are formed as sectors of the chopper wheel and the reflexion surfaces of the mirrors are perpendicular to the rotation axis of the chopper wheel.

Since no beam splitter is used for the transmission side beam combination and the receiver side beam separation by the measurement apparatus in accordance with the invention no intensity losses brought about thereby can consequently arise. The optical assembly can be of very simple design. Separate receivers are used for the detection of the light of the two light sources having different wavelengths, for example IR light, on the one hand, and UV light, on the other hand. The separate receivers can be specifically matched to the corresponding wavelengths to be detected by wavelength selecting elements, whereby the light yield of the receiver can be ideally configured.

A further advantage is that a measurement apparatus with two spectral channels is created by the invention in which the light sources can be operated permanently and thus temperature-dependent stability problems can be reduced.

The chopper wheel construction is very simple. It is made as a simple blade with mirrored areas as mirrors and with cut-outs. This is not only more stable, less complex and less expansive than the chopper apparatus known from U.S. Pat. No. 3,819,277 but also the optics of the measurement device can be adjusted more easily.

In a first embodiment a coaxial beam guidance takes place, this means that the transmission light path and the reception light path can be of coaxial design, at least within the measurement path. This is advantageous, since then the transmission unit and the receiver arrangement can be arranged at a side of the measurement path. For this purpose a retroreflector is arranged behind the measurement path which reflects the light into itself. Then a beam splitter is required in order to separate the transmission light path and the reception light path.

Advantageously the measurement apparatus in accordance with the invention is used when one of the light sources transmits UV light and the other light source transmits IR light, i.e. the two wavelengths are separated from one another very far. The receiver respectively associated with one wavelength is correspondingly configured for the purpose of receiving the UV light and/or the IR light respectively.

In a manner as simple as possible from a construction point of view, the chopper apparatus is configured point-symmetrical with respect to its axis of rotation.

In an embodiment of the invention the chopper apparatus is configured as a chopper wheel. The sectors highly reflecting for the one wavelength range are diametrically arranged for the deflection of the light of the corresponding light source. In the circumferential direction the chopper wheel has apertures between the highly reflecting regions for allowing the light from the other light source to pass through.

A simple assembly which is easy to realize having regard to the measurement apparatus results then when the optical axes of the light sources are arranged perpendicular to one another.

A particular advantage for an advantageous zero point correction is achieved in an embodiment of the invention.

In general, zero point corrections were very expensive in optical gas detection equipment. The zero stability must be checked regularly. This includes a so-called "bright measurement" without the light running through the measurement path. In this connection, the spectral characteristics of as many internal optical elements as possible are to be checked. Spectral drift and/or sensitivity of the detectors can be checked. Previously, this was complicated because the zero point correction was performed by pivoting a zero point reflector into the light beam at that point where the light beam exits the device and before it could enter the measurement path. The (external) measurement path is "turned off" so to say. This procedure has been carried out by pivoting the zero-point reflector by means of a mechanism and a motor, which both required installation space, other mechanical parts, a motor with control and which is subject to wear and failure.

The zero point correction can now be done much easier with the invention. For this purpose, the light of the first light source is used for zero point correction in those measuring phases in which the light of the other second light source is used for measuring and vice versa. Through customized analysis of the measured signals, the zero point correction can then be done. Pivoting a separate zero point reflector into the light beam with the described disadvantages is completely eliminated.

A simple mirror is provided for this purpose, with which at one time the light of the first wavelength range is deflected into the corresponding receiver while bypassing the measurement path and at other times the light of the other wavelength range is guided to its corresponding receiver while bypassing the measurement path. Which light is guided depends on the rotational position of the chopper wheel.

The light is not "lost", because either it is directed into the measurement path and is used for gas concentration measurement, or it is used for zero point correction.

In the following the invention will be described in detail by means of embodiments with reference to the drawing. In the drawing there is shown:

FIG. 1A a schematic illustration of a first embodiment of the measurement apparatus in accordance with the invention;

FIG. 2A a top view onto a chopper wheel of the first embodiment;

FIG. 1B a schematic illustration of the first embodiment of FIG. 1A with additional features for zero point correction;

FIG. 2B a top view onto a chopper wheel for the embodiment of FIG. 1B;

FIG. 3 a schematic illustration of another embodiment.

The measurement apparatus 100 in accordance with the invention for the determination of gas concentration comprises a first light source 102 and a second light source 104 which transmit light of different wavelength ranges into a measurement path 114. For example, the first light source 102 transmits UV light (ultraviolet light), which is illustrated in FIG. 1A by more pronounced (longer) dashed lines 106, and the second light source 104 transmits IR light (infrared light), which is illustrated in FIG. 1A by finer (shorter) dashed lines 108. The measurement apparatus 100 thus has two spectral channels.

The measurement apparatus 100 further comprises a chopper apparatus 110 which will be explained in the following text in more detail. The chopper apparatus 110 has the effect that the UV light 106 is alternatingly allowed to pass through in accordance with the position of rotation or the IR light 108 is deflected in order to thus arrive at the same optical path 112 at a measurement path 114, whereby a combination of the spectral channels onto the same optical path is brought about. In the embodiment in accordance with FIG. 1A the chopper apparatus 110 is arranged in such a way that the IR light 108 is deflected by 90°, wherein the optical axes of the light sources 102 and 104 are arranged perpendicular to one another.

The actual reaction of the light with the measurement gas takes place at the measurement path 114, with the measurement gas (the measurement gas being illustrated by points 116 in FIG. 1A) being provided in the region of the measurement path and from which concentrations of certain components should be determined. In this connection the measurement gas can be present in a non-illustrated measurement cuvette or the like—or also in a free path of an exhaust gas passage. One window 120 of a possible measurement cuvette is merely indicated in FIG. 1A.

From the point of view of the light sources a retroreflector 118 is present behind the measurement path 114, the retroreflector 118 reflecting the UV light and the IR light into itself in such a way that it passes through the measurement path 114 along the same optical path 112 one more time. The transmission light path and the reception light path are in this way configured coaxially at least within the measurement path 114 which is true for both wavelength ranges.

In order to separate the transmission light and the reception light a beam splitter 122 is provided which deflects the reception light, for example by 90°, into a direction of a receiver arrangement 124 which receives the light 106 and 108 of the light sources 102 and 104 respectively. For this purpose the receiver arrangement 124 has a first light receiver 126 which is associated with the first light source 102, this means that it can detect the UV light 106 from the first light source 102. Furthermore, the receiver arrangement 124 has a second receiver 128 which is associated with the second light source 104 and which is configured for the reception of the IR light 108 from the second light source 104.

Both the UV light 106 as well as the IR light 108 are incident at the receiver arrangement 124 from the same optical path. By means of the chopper apparatus 110 which is also part of the receiver arrangement 124, an optical separation of the spectral channels from UV light and IR light takes place. This separation takes place in a manner analog to the combination, this means that the UV light is allowed to pass through onto the first receiver 126 in accordance with the position of rotation and the IR light is deflected for a different position of rotation by 90° onto the second receiver 128.

For this purpose the chopper apparatus 110 is configured as a chopper wheel 130 which rotates about an axis 132. As is illustrated in FIG. 2A, the chopper wheel 130 has highly reflecting sectors 134 for the one wavelength range—in this example for the IR light 108—with a plurality of (at least two) sectors being respectively diametrically arranged. Since the mirrors are formed as sectors of the wheel, the mirror surfaces are lying perpendicular to the axis of rotation 132 of the chopper wheel 130. Sectors 134 are located on approximately the same part circle, which are formed as simple cut-outs 136 and can be produced, for example by punching. The mirrors 134 are preferably prepared by vapor deposition of a reflective mirror layer on the chopper wheel in the corresponding sector.

In this way the following functional principle results: When the chopper wheel 130 takes on one position of rotation in which the reflecting sectors 134 are present in the optical path (FIG. 1A) the UV light 106 is deflected, this means that it is blocked for the measurement path 114 and the IR light 108 is deflected from the transmission side into the measurement path 114 and at the same time is deflected onto the second receiver 128 at the receiver side by means of the sector 134 disposed opposite. When the chopper wheel 130 takes on a position of rotation in which the sectors 136 are present in the optical path the IR light 106 is not deflected into the common optical axis at the transmission side and is either lost or is used for other purposes. The UV light 106 is likewise also allowed to pass through on the transmission side and arrives at the measurement path 114 along the same optical path as previously the IR light. On the receiver side the UV light is again allowed to pass through and is incident at the first receiver 126.

Finally, an evaluation of the received signals and therefrom a determination of a gas concentration takes place in an evaluation unit 140 to which the two receivers 126 and 128 are connected. This preferably takes place using a Lock-In method.

FIG. 1B shows an embodiment similar to FIG. 1A, wherein in addition, a further deflecting mirror 150A is provided. This mirror 150A is used for deflecting that light that is not being used for measuring in dependence of the position of a chopper wheel 130A. The chopper wheel 130A of this embodiment is shown in FIG. 2B. It must also be able to generate dark periods in which no light reaches the receivers 126 and 128, so that the lock-in method can be used for evaluation. Therefore, it comprises sectors 138a, which simply block both the UV light 106 and IR light 108. Those sectors 138a are provided in addition to the reflection mirrors 134A and the cut-outs 136A for transmission of light. The individual sectors, namely mirrors 134A, cut-outs 136A and sectors 138A are arranged symmetrically.

Thus, when the UV light 106 is transmitted through the cut-outs 136A of the chopper wheel 130A it enters the measurement section 114, the IR light 108 is guided to the deflecting mirror 150A and directed to the associated receiver 128. It bypasses the measuring section 114. Thereby, it is transmitted by the chopper wheel 130A a second time.

An analog result is obtained for an angular position of the chopper wheel 130A at which the mirrors 134A are located in the beam path. Then, the IR light 108 is directed into the measurement section 114 and the UV light 106 to the reflecting mirror 150A and further via the second mirror 134A to the associated receiver 126. Now, the UV-light 106 bypasses the measuring section 114.

It is understood that the mirrors 134A need to be reflective on both sides so that on one side the infrared light 108 and on the other side the UV light 106 is reflected. In addition, the evaluation unit 140 has to be arranged for a corresponding zero-point correction. The individual signals can be separated via time division multiplexing and analyzed by means of the lock-in technique. Whenever the intensity of the light through the measurement path is measured with a receiver, the other receiver registers the intensity over the reference path, which is the intensity of the light that bypasses the measuring section via the deflecting mirror 150A.

In another embodiment 300 in accordance with FIG. 3, a different angular arrangement of the two light sources 302 and 304 with respect to one another, of the two receivers 326 and 328 with respect to one another and correspondingly of the chopper wheel is illustrated in contrast to the first embodiment 100. Thus, also other right-angled arrangements are possible. Thereby, possibly other forms of construction of the overall measurement apparatus 300 can be realized. In turn the combination and separation of the spectral channels takes place just like in the first and second embodiments.

What is claimed is:

1. A measurement apparatus having two spectral channels for the determination of gas concentrations comprising:
   a first and a second light source (102, 104; 302, 304) which transmit light of different wavelength ranges into a measurement path (114);
   a receiver arrangement (124) which receives the light from the light sources (102, 104);
   a chopper apparatus (110) which has two reflecting mirrors (134; 134A) for one of the wavelength ranges and two cut-outs (136; 136A) between the mirrors on the same part of a circle in the circumferential direction in order to alternately allow the light from the light sources to pass through and/or to deflect the light from the light sources (102, 104) respectively in order to bring the light via the same optical path into the measurement path (114); and an evaluation unit (140) for the evaluation of the received signals and for the determination of a gas concentration therefrom, wherein the receiver arrangement (124) has a first and a second receiver (126, 128; 326, 328), with the first receiver (126, 326) being associated with the first light source (102) and the second receiver (128; 328) being associated with the second light source (104) for the reception of the light of a corresponding wavelength range; and wherein the chopper apparatus (110) is also a part of the receiver arrangement (124) and the chopper apparatus (110) separates the light from the same optical path (112) following a passage along the measurement path (114) by deflection of light and/or by allowing the light to pass through and associates this with the corresponding receiver (126 or 128 respectively; 326 or 328 respectively) characterized in that the chopper apparatus (110) is designed as a single chopper wheel (130; 130A) and the mirrors (134; 134A) are formed as sectors of the chopper wheel (130; 130A) and the reflexion surfaces of the mirrors are perpendicular to the rotation axis of the chopper wheel (130; 130A).

2. The measurement apparatus in accordance with claim 1, characterized in that the mirrors are made by vapor deposition of a reflexion surface on the chopper wheel.

3. The measurement apparatus in accordance with claim 1, further comprising a retroreflector arranged behind the measurement path, wherein a transmission light path and a received light path are configured coaxial and a beam splitter separates the transmission light path from the reception light path.

4. The measurement apparatus in accordance with claim 1, wherein one of the light sources transmits UV light and the other light source transmits IR light and wherein the respectively associated receiver is configured to receive the UV light and the IR light respectively.

5. The measurement apparatus in claim 1, wherein the chopper wheel is configured point-symmetrically with respect to its axis of rotation.

6. The measurement apparatus in accordance claim 1, wherein the mirrors and the cut-outs are arranged diametrically to each other.

7. The measurement apparatus in accordance with claim 1, wherein the light sources each have an optical axis and the optical axes of the light sources are arranged perpendicular to one another.

8. The measurement apparatus in accordance with claim 1, wherein the light of the first or second light source is used for zero point correction in those measuring phases in which measurement is done with light of the other light source, respectively.

9. The measurement apparatus in accordance with claim 1, wherein a deflection mirror is provided with which the light of both wavelength ranges is deflected into the corresponding receivers while bypassing the measurement path.

* * * * *